United States Patent [19]

Bodó et al.

[11] Patent Number: 4,925,878
[45] Date of Patent: May 15, 1990

[54] METHOD TO PREVENT SEASICKNESS

[75] Inventors: György Bodó; József Knoll; Éva Somfai; Sándor Virag; Ferenc Zák, all of Budapest, Hungary

[73] Assignee: Chinoin Gyogyszer- Es Vegyeszeti Termekek Gyara Rt., Budapest, Hungary

[21] Appl. No.: 273,851
[22] PCT Filed: Dec. 18, 1987
[86] PCT No.: PCT/HU87/00058
  § 371 Date: Aug. 17, 1988
  § 102(e) Date: Aug. 17, 1988
[87] PCT Pub. No.: WO88/04552
  PCT Pub. Date: Jun. 30, 1988

[30] Foreign Application Priority Data

Dec. 19, 1986 [HU] Hungary .............................. 5338/86

[51] Int. Cl.$^5$ ............................................. A61K 31/135
[52] U.S. Cl. ................................................... 514/646
[58] Field of Search ........................................... 514/646

[56] References Cited

FOREIGN PATENT DOCUMENTS 1031425 6/1966 United Kingdom .
1153578 5/1969 United Kingdom .

OTHER PUBLICATIONS

Martindale, The Extra Pharmacopoeis 28th Ed., (1982), pp. 1752-1753.
N. Negwer "Organisch-Chemische Artzneimittel und ihre Synonyma" 5th Edition, 1978.

Primary Examiner—Stanley J. Friedman
Attorney, Agent, or Firm—Herbert Dubno; Jonathan Myers

[57] ABSTRACT

The compounds of the Formula I

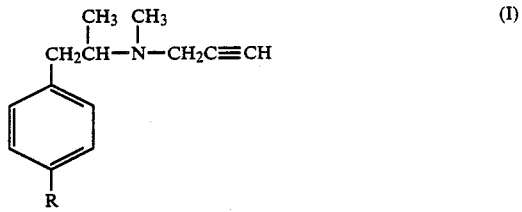

(wherein R is hydrogen or halogen) and pharmaceutically acceptable acid addition salts thereof are suitable for the prophylaxis of undesired and unfavorable symptoms (e.g. perspiration, nausea, vomiting, dizziness, etc.) which occur when healthy humans or mammal animals are subjected to unusual moving (e.g. during transportation on aeroplane, or vehicles, ships, etc.)

1 Claim, 1 Drawing Sheet

METHOD TO PREVENT SEASICKNESS

FIELD OF THE INVENTION

The present invention relates to a "stewardess" composition suitable for the prevention of disadvantageous physiological symptoms occurring during unusual external movement (such as transportation) of healthy humans and mammal animals containing a compound of the general Formula I

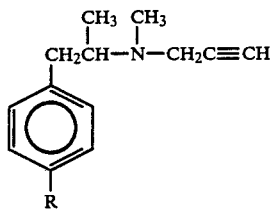

(wherein R stands for halogen or hydrogen) in an oral dosage form, optionally admixed with additives such as carriers, diluents, flavorants and/or coloring and aromatizing agents, and to a process for the preparation thereof and to the use thereof.

BACKGROUND OF THE INVENTION

It is known that on subjecting humans or certain mammals (e.g. dogs, cats) to long-lasting external moving or transportation accompanied by unusual or special movements (such as shaking, waving, unusual atmospheric conditions, great acceleration, uneven road conditions, etc.) characteristic undesired and unfavorable physiological symptoms occur.

The above symptoms are generally called "sea disease" or "air sickness" ("nausea maris", kinetosis, carsickness, etc.). This is however no real disease but a physiological symptom complex which occurs with humans under certain conditions. The symptoms depend on the individual and his (or her) antecedents, training, habits and biological condition. The symptoms can be observed mainly portation in air or sea travel but in case of certain persons they occur also when travelling by motorcar, bus, train or riding, in an elevator, on a cable railway, etc.

It is unnecessary to discuss the disadvantages of this condition in details. Persons driving in heavy traffic are very often subjected to this condition which is extremely disadvantageous and dangerous in cases when the person has to work during transport or traffic or soon afterwards. Thus vehicle drivers, air pilots, spacemen, astronauts, aircraft staff members or sportsmen, commercial travellers, businessmen, etc. who must exhibit high-level and concentrated intellectual or physical activity are badly in need of the prophylaxis of "kinetosis". This need has so far not been duly satisfied.

Similarly there is a demand for the prophylaxis of undesired symptoms which occur on the transportation of mammal animals (e.g. hygienic transportation of animals, etc. after the termination of transportatio etc.).

Compositions comprising scopolamine (L-6,7-epoxy-tropine-tropate) were the first preparations used for the propylaxis of sea-sickness. This alkaloid is however a strong parasympatholytic which causes visual disturbances, stupor, muscular weakness, dryness of mouth and the use thereof is dangerous. Recently attempts have made to eliminate certain undesired side effects of scopolamine by administering the same intradermally (Aviat, Space Environ. Med. 54 (II) pages 984–1000).

The other generally used composition (Dymenhydrinate[x]) comprises the 8-chloro-theophyllin salt of N,N-dimethyl-2-(diphenylmethoxy)-ethyl-amine as active ingredient (Daedalon[R]; J. Am. Med. Assn. 160, pages 755–760). The use of this composition involves fewer hazards but the said composition exhibits very unfavorable hypnotic sedative effects. Daedalon effects working capacity and performance during transportation or thereafter in an undesired manner, and moreover in certain cases makes the same even impossible.

It is known furtheron that Cavinton[R] (comprising as active ingredient Vinpocetin[x]) decreases the affinity for kinetosis (Bodó, Hartman: Therapia Hungarica 27.2 (1979.)). The drawback of Cavinton[R] is that the effect is exerted only 5–7 days after administration.

The basic factors of the neurophysiology of the kinetosis are as follows:

The vestibular receptor, the retina and the somatosensorial receptors are unusually stimulated by the movement and weightlessness. The various structures react pathologically upon the unusual stimuli in the central nervous system. The reaction of the CNS is vertigo, nausea, head-ache and sleepiness. The reaction of the limbic system results in depression. The hypothalamus induces through the hypophysis an increased production of ADH, ACTH, GH, PRL. The vestibular cerebellum causes through the vegetative nervous system cold sweat, pallor, reduced stomach motility and cardiovascular and respiratory disorder. the vestibular cerebellum causes vomiting as well due to Parvicellularis Reticularis Formatio (Brain Res. 270: 154–158.)

The point of attack of drugs acting against kinetosis has not been determined exactly. Effective agents are the centrally attacking anticholinergic hyoscin and the adrenergic ephedrine and amphetamine. The activity of the phenothiazine blocking dopamine $D_2$ receptors in the chemoreceptor trigger zone is very weak. Effective preventing agents are other antihistamines, such as dimenhydrinate, cyclizin and cinnarizene. As a peripherally acting agent domperidon can be mentioned.

OBJECT OF THE INVENTION

It is the object of the invention to provide a composition for preventing "sea sickness" which acts rapidly without showing any undesired side effects and without deteriorating psychical activity.

DESCRIPTION OF THE INVENTION

The present invention relates to a composition suitable for the prophylaxis of undesired and unfavourable physiological symptoms which occur when healthy humans or mammal animals are subjected to unusual external moving (e.g. transportation). The invention relates to the preparation and use of said composition as well.

The composition according to the present invention comprises as active ingredient a compound of the Formula I in an oral dosage form optionally in admixture with suitable additives, carriers, aromatizers, flavorants and/or colorants.

The compositions are prepared by simple admixture of the components.

A particularly preferred representative of the active ingredients of the Formula I is the compound of the Formula IA (Selegilinum[x]).

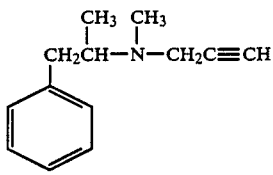

(IA)

The active ingredients and the processes for the preparation thereof are disclosed in Hungarian patent specifications Nos. 151,090, 154,655 and 167,755.

The use of the said compounds as psycho-stimulant, antidepressant, catabolic and slimming agents is described in Hungarian patents No. 151,090. The optically active antipodes and use as MAO inhibitor are set forth in Hungarian Patent No. 154,655.

The preferred dose of the compositions of the present invention is in each case about 10-20 mg of active ingredient of the Formula I. On administering the composition at a single dose of 10-20 mg every 24th hour an agreeable general condition can be observed and the previously mentioned undesired symptoms occurring due to unusual moving conditions (transportation) disappear during a long journey.

The composition of the present invention can be particularly advantageously used by passengers and drivers of aeroplanes and other vehicles (motorcars, ships, air-ships, etc.).

The composition of the present invention is highly suitable for administration to children subjected to unusual transportation conditions (aeroplane, ship).

The single dose on children amounts to 3-5 mg, depending on the bodyweight for 24 hours.

The active ingredient can be encapsulated per se optionally without any carrier. The desired amount of the active ingredient filled into gelatine capsules can be directly consumed. The present invention encompasses however all oral dosage forms, i.e. all forms suitable for oral administration.

According to a preferred embodiment of the invention the active ingredient of the Formula I is finished in the form of a dragée or tablet coated by sugar or chocolate.

The active ingredient is incorporated into the core.

The composition of the present invention may be finished in the form of one of the following preparations: hard sweets (drops), fondant; sweets, nugates, marzipan optionally candied or coated by chocolate: mixed sweets, caramella, dragées, coated dragées and (particularly for children) chewing gum, syrup and dry syrup.

The additives are determined by the appearance form of the composition. Thus conventional and generally used additives of sweets' industry can be used (e.g. saccharose and starch liquor). The compositions of the present invention are prepared by methods of sweets' industry known per se. The active ingredient of the Formula I is generally dispersed in the warm composition.

As flavorants conventional additives of sweets' industry can be used, e.g. sacharose, dextrose, fructose, malt sugar, lactose, mannitol, sorbitol, saccharine, dulcitol, cyclamate, honey, sweetroot extract, coffee, tea- and cocoa-extract, orange-extract, extract and aroma of other fruits, citric acid, tartaric acid, lactic acid.

The composition comprises conventional flavorants applicable and licensed in sweets' industry, e.g. tarrazine, acid-yellow, amaranth, neucoccine, indigo-carmine, brillant black and carbon powder (carbo medicinalis).

The composition may also comprise preservatives and as further active components vitamins, particularly vitamin $B_6$ and vitamin C. Compositions comprising a vitamin additive maintain the high activity particularly on long-lasting application.

The above compositions may be preferably prepared by dissolving the active ingredient in an aqueous solution of sugar, and adding the flavorants and diluents. One may also proceed by adding to the mixture a binding agent suitable for human consumption (e.g. gum accacia) and an acceptable lubricating agent (e.g. stearic acid or a salt thereof).

The active ingredients of the prophylactic compositions of the present invention can be prepared by known methods disclosed in Hungarian patents Nos. 151,090, 154,655, 187,755 and Hungarian patent application Ser. No. 2124/84.

The compounds of the Formula I comprise an asymmetrical carbon atom and may form optically active antipodes. The present invention encompasses compositions comprising optically active forms of the compounds of the Formula I.

The preparation of the optically active compounds is described in Hungarian patents Nos. 154,655, 187,755 and Hungarian patent application No. 2124/84.

The compounds of the Formula I can be prepared preferably by reacting a 2-phenyl-isopropyl-derivative of the Formula II

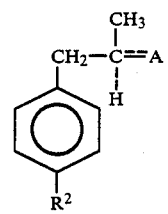

(II)

with a compound of the Formula III

B—R$^1$ (III)

wherein

R$^1$ stands for methyl or propynyl or a radical which can be transformed into methyl and propynyl, respectively;

R$^2$ stands for hydrogen or halogen or a radical which can be converted into halogen;

A and B stand for radicals which on reacting with each other are capable of forming a bivalent radical of the Formula

or comprise the said radical; and A is attached to the carbon atom by a single or double bond (in the latter case it can not bear a hydrogen atom)

if desired introducing the R$^2$ halogen substituent into the amine of the Formula V

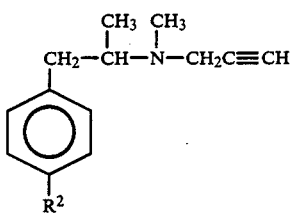
(V)

thus obtained; and if desired forming the propynyl radical in the amine of the Formula IV

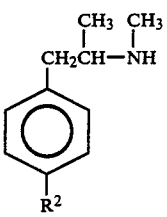
(IV)

in one or more steps; or N-methylating a compound of the Formula XIV

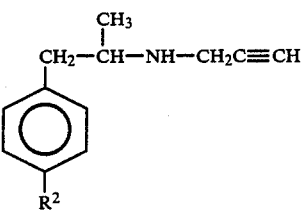
(XIV)

whereby the order of succession of the last three steps can be changed.

The propylamine of the Formula I can be converted into an acid addition salt formed with a mineral acid or organic acid.

One may also proceed by reacting an amine of the Formula VIII

(VIII)

wherein
R$^4$ stands for an optionally halogeno substituted and/or unsaturated propyl or hydrogen and
R$^5$ represents hydrogen or methyl with a phenyl acetone derivative of the Formula IX

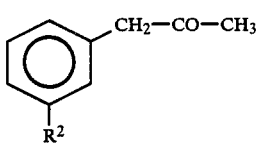
(IX)

(wherein
R$^2$ is as stated above) reducing the ketimine or oxyamine thus obtained and if desired converting the R$^4$ group into propynyl and/or the R$^5$ group into methyl, in any order of succession.

One may also proceed by reacting an amine of the Formula VIII with a phenyl isopropyl amine of the Formula XI

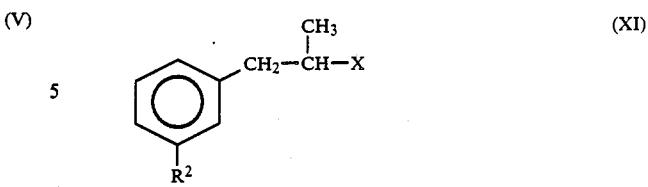
(XI)

(wherein X stands for halogen or a sulfonic acid ester group) and if desired converting the R$^2$ group into halogen, the R$^4$ group into propynyl and/or the R$^5$ group into methyl, in any order of succession.

According to a preferred form of realization of the process the amine of the Formula XII

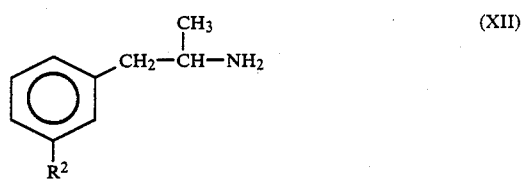
(XII)

is subjected to methylation and propynylation in any order of succession or condensing an amine of the Formula IV with formaldehyde and acetylene. Propylation may also be carried out stepwise through a halogenopropyl and propenyl group, respectively. Thus one may proceed by reacting the amine of the Formula XII with 1,2-dibromo-propene and converting the 2-bromopropenyl derivative thus obtained into the propynyl derivative by thermal treatment or reaction with a base.

One may also proceed by reacting an amine of the Formula XIV

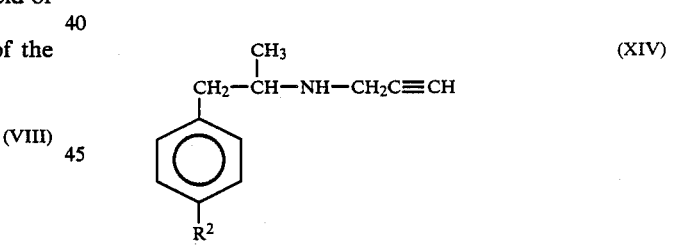
(XIV)

with a methylating agent or with formaldehyde and formic acid. The above mentioned methylation can be accomplished with the aid of dimethyl phosphate, methyl halide, dimethyl sulfate or methyl sulfuric acid.

As an example for the introduction of the halogen atom the following method is mentioned:

In a compound of the Formula VI

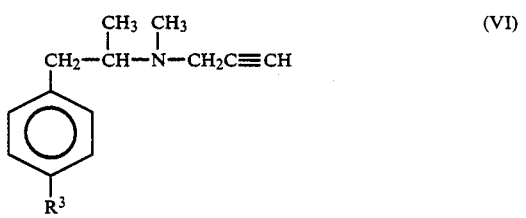
(VI)

or of the Formula XIII

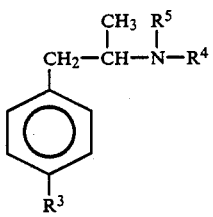

(XIII)

(wherein $R^3$ is nitro, amino or diazonium) the nitro group is reduced to amino and the latter is transformed into diazonium-fluoro-borate and thus a fluorine atom is introduced in the place of $R^3$.

Optically active derivatives are prepared by using as starting material an optionally active compound of the Formula II, IV, V, VII

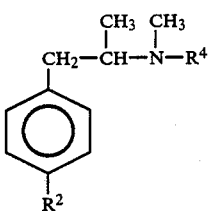

(VII)

and of the Formula XI or XIV or subjecting a compound of the Formula I or VI to resolution by forming diastereomeric pair of salts by reacting with an optically active acid.

The compositions of the present invention may comprise the compound of the Formula I in the form of a pharmaceutically acceptable acid addition salt thereof (e.g. hydrochloride, hydrobromide, sulfate, phosphate, acetate, formate, maleate, tartarate, lactate, 3,5-dinitrobenzoate, citrate, or (preferably) ascorbinate, oxalate, etc.).

Further details of the present invention are to be found in the following Examples without limiting the scope of protection of the said Examples.

EXAMPLE 1

Circular or angular pastilles weighing 1.3 g having the following composition are prepared:

| Component: | Amount: |
| --- | --- |
| (−)-N-methyl-N-propargyl-(2-phenyl--1-methyl)-ethyl-amine-hydrochloride (Selegilinum* hydrochloride) | 10 mg |
| Saligenin | 50 mg |
| Carbowax 6000 | 40 mg |
| Magnesium stearate | 7 mg |
| Tragacanth | 58 mg |
| Tartaric acid | 13 mg |
| Flavoring aromatics | 0.004 ml |
| Sugar varnish ad | 1.3 g |

The basic sugar varnish and tartaric acid are thoroughly admixed, whereupon the active ingredient, saligenin and Carbowax dissolved in a small volume of alcohol is added. The mixture is thoroughly homogenized and dried. The dry mixture is passed through a sieve size 40, the tragacanth is added, the mixture is thoroughly homogenized and granulated by adding a small amount of syrup. The granulate is dried at 30°–40° C., the flavoring aromatics are added and the mixture is allowed to stand in a closed container overnight. After addition of magnesium stearate the mixture is pressed to pastilles in a suitable apparatus.

EXAMPLE 2

Sweets (drops) having the following composition are prepared:

| Component: | Amount: |
| --- | --- |
| Sugar | 20.25 kg |
| Liquid glucose | 9.45 kg |
| Tartaric acid | 255 g |
| Active ingredient | 16.38 g |
| Amyl-m-cresole | 13.6 g |
| Flavoring aromatics | according to taste |
| Coloring solution | according to taste |
| Water | as required |

The sugar and liquid glucose are added to a suitable volume of water and the syrup of suitable consistance thus obtained is heated to boiling. To the hot syrup the tartaric acid and the coloring agent are added, the mixture is cooled to 60° C. whereupon the active ingredient, amyl-m-cresol and the flavoring agent are added. The liquid syrup is carefully stirred and passed through a sugar-forming apparatus. Thus drops comprising 10 mg of the active ingredient are obtained.

EXAMPLE 3

Preparation of tablets which can be coated with a sugar varnish and are suitable for the manufacture of dragées.

The following materials are used:

| Component: | Amount: |
| --- | --- |
| (−)-N-methyl-N-propargyl-(2-phenyl-1--methyl)-ethyl-amine-hydrochloride | 5 kg |
| Powdered polyvidone | 9 kg |
| Potato starch | 35 kg |
| Lactose | 84 kg |
| 96% ethanol | 80 l |
| Water | 17 l |

The sieved components are homogenized in a mixer, granulated with aqueous ethanol and dried at 60° C. After re-granulation the granules are homogenized in a fluid apparatus and the ready granules are stored in a container. The mixture can also be pressed to 10 mg tablets in a Fette P XXXI tabletting machine.

EXAMPLE 4

The following components are admired:

| Component: | Amount: |
| --- | --- |
| (−)-N-methyl-N-propargyl-[2-(4-fluorophenyl)-1-methyl]-ethyl-amine-hydrochloride | 10 g |
| Talc | 7 g |
| Magnesium stearate | 5 g |
| Polyvidone | 20 g |
| Potato starch | 100 g |
| Lactose | 150 g |

The components are homogenized and from the mixture 1000 tablets are pressed in an analogous manner to the previous Examples.

EXAMPLE 5

Chewing gums (about 10 g) having the following compositions are prepared:

| Component: | Amount: |
|---|---|
| (±)-N-methy-N-propargyl-(2-phenyl-1-methyl)-ethyl amine hydrochloride | 0.02 g |
| Natural caoutschouc/purified/ | 2.8 g |
| Dextrose | 2.8 g |
| Caramelle paste | 0.2 g |
| Powdered sugar | 11.4 g |
| Aroma | according to taste |

The natural caoutschouc, caramelle paste and powdered sugar are kneaded and the solution of the active ingredient, liquid dextrose and aroma is added under constant stirring. The mixture is thoroughly homogenized, dried in the form of strips, cut to pieces weighing about 10 g and packed.

EXAMPLE 6

Activity tests

Human tests are carried out on healthy young men aged 18–23 years. The physical condition of the candidates is controlled by suitable basic tests; blood pressure, pulse, attention examination test; whereupon the candidates are stimulated according to the method of Coriolis (see Voenno Med. Zs. (1966), 9, page 59).

The tests are carried out under usual conditions:
a consent is obtained;
the sufficiency of the equilibrium system is checked by ear-nose-throat and other examinations;
the psychological performance is determined by means of the "Révész Nagy" attention-examination test ("Psychologiai Tanácsadás a pályaválasztásban, Módszertani füzetek, 11., page 5; edited by Országos Pedagógiai Intézet Budapest (1982)).

The composition prepared according to Example 3 comprising 20 mg of Selegilinum$^x$ is tested and compared with placebo and Daedalon. In the case of each individual the period lapsed between the beginning of the Coriolis stimulus and the occurence of string nausea ("resistance time") is determined. The compositions are administered orally, to three groups:
11 humans receive 20 mg of Selegilinum-hydrochloride;
11 humans obtain placebo in the same dose;
11 humans are treated with 2 Daedalon tablets (totally 100 mg).

Figure 1:
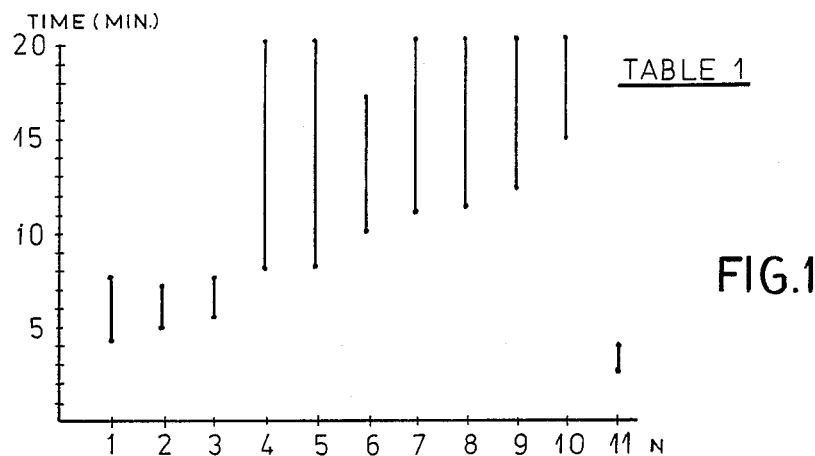
FIGS. 1, 2 and 3 are respectively a series of three tables, designated Tables I, II and III. Each of the tables is a bar graph. The data in Table I relate to treatment of patients with Selegilinum HCl of the Formula (I) of the invention, the data in Table II relate to treatment with a placebo, and the data in Table III relate to treatment with Daedalon, an established compound in the prevention of motion sickness. In each table, the X-axis designates each of 11 patients tested and the Y-axis indicates the time in minutes it takes for motion sickness to occur during the test. The arrow at the end of each bar shows the time it takes for motion sickness to occur after administration of either Selegilinum HCl, the placebo or the Daedalon, respectively. The opposite end of each bar graph from the arrow shows the time it takes for motion sickness to occur without prior administration of any of the above. In each case motion sickness is induced according to the procedure set forth in Example 6, hereinafter.
Figure 2:
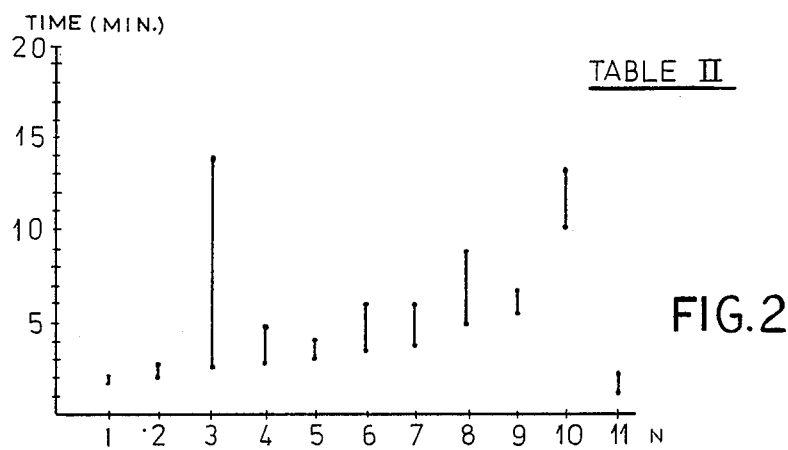
Figure 3:
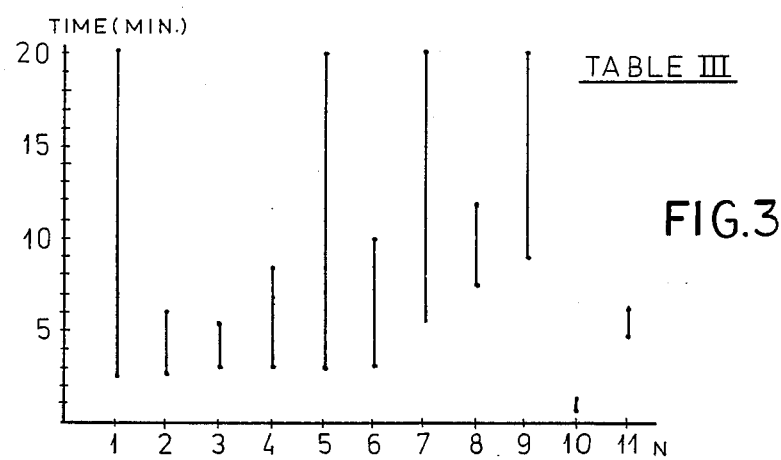

Two hours after the administration of the test composition the Coriolis stimulus is repeated and the resistance time is determined. The attention examination test is accomplished after the first and second Coriolis stimuli. The results are summarized in FIGS. 1, 2 and 3 in Table form.

The resistance time is plotted on the vertical axis, in minutes. On the horizontal axis 11 humans are represented side by side. The direction of the arrow appearing on the Tables shows the change caused by the treatment: The starting point of the arrow shows the vegetative resistance time without influencing the organism while the end-point of the arrow indicates the resistance time after administration of various test substances (the upward arrow shows the improvement while the downward arrow the deterioration—in one case each).

Table I shows the results obtained with Selegilinumhydrochloride, Table II indicates those obtained with a placebo and Table III contains the results obtained with reference compound Daedalon.

Evaluation of the Test

| I. Selegilinium-hydrochloride | | |
|---|---|---|
| before: $\bar{X} = 8.58$ <br> $S = 3.65$ | after: $\bar{X} = 14.68$ <br> $S = 6.97$ | $T = -2.568$ <br> significant |

It can be seen that the resistance time is improved from 8.58 minutes ($T = -2.568$). Thus the improvement is significant.

| II. Placebo | | |
|---|---|---|
| before: $\bar{X} = 3.87$ <br> $S = 2.33$ | after: $\bar{X} = 6.25$ <br> $S = 4.18$ | $T = -1.64$ <br> significant |

In the case of the placebo the resistance time increases from 3.87 minutes to 6.25 minutes ($T = -1.64$) and this is not significant.

| III. Daedalon | | |
|---|---|---|
| before: $\bar{X} = 4.4$ <br> $S = 2.54$ | after: $\bar{X} = 11.53$ <br> $S = 7.3$ | $T = -3.858$ <br> significant |

The resistance time is increased from 4.4 minutes to 11.53 minutes/$T = -3.058$/, i.e. the change is significant.

In order to establish whether the difference between the activity of Seligilinum and Daedalon is significant, the following calculations are carried out:

| | |
|---|---|
| $\bar{X} = 6.1$ <br> $S = 4.23409$ <br> $F = 20$ <br> $P(5\%) = 2.886$ <br> $T = 0.427622$ | $\bar{X} = 7.13$ <br> $S = 6.7743$ |

Thus as far as the resistance time is concerned there is no significant difference between the said two compositions.

The attention examination test shows no significant change between the two compositions.

The subjective examinations reveal however the following results:

placebo results in no change at all;
under the effect of Daedalon the test persons become sleepy, tired and fall asleep after the test;
under the effect of Selegilin the general condition becomes pleasant ant the test persons do not get sleepy.

An unambigous explanation of the mechanism of effect of the composition according to the invention cannot be given yet. As according to observations in the literature the cerebral dopaminergic stimulation i.e. based on the known MAO-paralysing activity of Selegilinum does not act or only weakly on the kinetosis, we can give two explanations of the fact that the kinetosis induced by coriolis stimulus is significantly reduced by Selegilinum hydrochloricum:

(1) The increase of the dopamine level in the recently discovered Parvicellularis Reticularis Formatio, (PCRF) results in reducing vomiting. This would be the first medicine of this sort.

(2) Selegilinum hydrochloricum does not act by increasing dopamine level but by a different, so far unknown mechanism.

Preparation of the active ingredients

EXAMPLE 7

21.92 g of N-1-phenylisopropyl-N-methyl-2-bromopropenyl amine are dissolved in 320 ml of alcohol and 40 ml of a 50% aqueous potassium hydroxide solution are added. The mixture is refluxed for 216 hours. The alcohol is distilled off and to the residue water is added and the mixture is extracted with benzene. The benzene solution is dried over potassium carbonate and evaporated. The residue is distilled off in vacuo. At 104°–110° C., 5 Hgmm 15 g of N-1-phenylisopropyl-N-methyl-propynylamine are obtained as a main fraction. $n_D^{20.4} = 1.5229$.

The base thus obtained is converted into the hydrochloride by using anhydrous alcohol containing hydrogen chloride. Mp.: 131°–131.5° C. (after recrystallization from a mixture of alcohol and ether).

EXAMPLE 8

7.-g (0.0443 mole) of (-)-N-methyl[2-(4-fluorophenyl)-1-methyl]-ethyl amine-$(\alpha)_D^{20} = -3.44°$ (ethanol) are dissolved in 60 ml of acetone, whereupon 28.9 g (0.21 mole) of potassium carbonate are added and a 60% toluene solution of 7.56 g (0.045 mole) of propargyl bromide is added dropwise under stirring. The reaction mixture is stirred at 35°–40° C. for 3–4 hours, filtered, washed with acetone and the filtrate is evaporated. The residue is distilled off at 2 Hgmm. 2 Hgmm. Thus 3.3 g of (−)-N-propynyl-[2-(4-fluoro-phenyl)-1-methyl]ethyl-amine are obtained, bp: 120°–122° C., $n_D^{20} = 1.5052$. The melting point of the hydrochloride amounts to 169°–171° C., $\alpha_D^{20} = -6.2°$ (c=2.4, ethanol); $\alpha_D^{20} = -10.98°$ (c=2.9, water).

EXAMPLE 9

10 g (0.065 mole) of 4-fluoro-phenyl-acetone and 5.3 g (0.097 mole) of propargyl amine are dissolved in 55 ml of 96% alcohol. After half an hour, 1.75 g of aluminium-foil activated with mercuric chloride are added at 60° C. and the mixture is allowed to stand overnight. To the reaction mixture 15 ml of 40% sodium hydroxide are added and the alcohol is distilled off. The residue is extracted with benzene. The benzene solution is extracted with 10% hydrochloric acid, the aqueous hydrochloric acid layer is made alkaline and extracted with benzene. The benzene phase is dried and evaporated. The residue is subjected to distillation in vacuo. Thus 4.9 g of (±)-N-propynyl-[2-(4-fluoro-phenyl)-1-methyl]-ethyl amine are obtained bp: 134°–140° C. (17 Hgmm), $n_D^{20} = 1.5031$, yield 36%.

4 g of the product thus obtained are dissolved in 25 ml of acetone, to the solution 4 g of potassium carbonate and 4 g of methyl iodide are added. The reaction mixture is refluxed for 2 hours, filtered and evaporated. The residue is dissolved in 10% hydrochloric acid, clarified, filtered, made alkaline with a 40% sodium hydroxide solution and extracted with toluene. The toluene solution is dried and acidified with ethanolic hydrogen chloride. The precipitated product is filtered and dried. Thus 3.1 g of (±)-N-methyl-N-propynyl-[2-(4-fluorophenyl)-1-methyl]-ethyl amine-hydrochloride are obtained, mp.: 131°–133° C.

EXAMPLE 10

29.8 g of d-phenylisopropyl-N-methylamine and 14 g of propargyl aldehyde are dissolved in 100 ml of alcohol. 7 g of aluminium foil are cut to small pieces and rinsed with alcohol free of fats whereupon a solution of 30 g of sodium chloride and 30 ml of water is poured on the aluminum foil. The mixture warms up and gas evolution begins. The solution is decanted after 6–7 minutes and the aluminum foils are washed with water.

The aluminum thus obtained is added to the above solution under stirring and cooling. During the addition the reaction mixture is cooled so that the temperature should be between 15° C. and 30° C. The reaction mixture is stirred for 24 hours, whereupon 60 ml of a 40% sodium hydroxide solution are added and the mixture is stirred for a further hour. The two layers are separated and the aqueous phase is extracted with benzene three times. The benzene extracts are united with the alcoholic phase and evaporated. The oily and aqueous layers formed are separated and the aqueous phase is extracted with benzene. The benzene extracts are united with the oil, dried over potassium carbonate and the benzene is removed. The residue is distilled off at 5 Hgmm. The d-phenylisopropyl-N-methyl-propynylamine main fraction distils off at 5 Hgmm, $n_D^{20.4} = 1.5175$; the hydrochloride melts at 131.5; $\alpha_D^{20} = +10.9°$.

What we claim is:

1. A method for preventing motion sickness which comprises the step of orally administering to a patient in need of said treatment a therapeutically effective amount of the compound of the Formula (I)

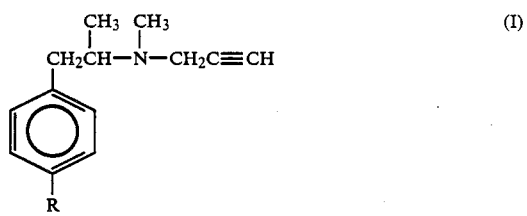

wherein R is hydrogen or halogen; or a pharmaceutically acceptable acid addition salt thereof.

* * * * *